United States Patent [19]

Moore

[11] Patent Number: Plant 6,703

[45] Date of Patent: Mar. 28, 1989

[54] GRAPEVINE — SATURN CULTIVAR

[75] Inventor: James N. Moore, Fayetteville, Ark.

[73] Assignee: University of Arkansas, Fayetteville, Ark.

[21] Appl. No.: 120,496

[22] Filed: Nov. 13, 1987

[51] Int. Cl.[4] ..... A01H 5/00

[52] U.S. Cl. ..... Plt./47

[58] Field of Search ..... Plt./47

*Primary Examiner*—James R. Feyrer

[57] ABSTRACT

Description and specifications of a new and distinct grapevine variety which originated from seed produced by a hand-pollinated cross of Dunstan 210 (non-patented) and New York Selection 45791 (non-patented) is provided. This new grapevine variety can be distinguished by its midseason ripening seedless fruit, its attractive red fruit color, its unique oval fruit shape, its very firm fruit texture, and its long-term storage capability.

2 Drawing Sheets

SUMMARY OF THE INVENTION

The new and distinct variety of grapevine originated from a hand pollinated cross of Dunstan 210 (non-patented)×New York selection 45791 (non-patented), made in 1971 at the Arkansas Agricultural Experiment Station experimental vineyard at Clarksville, Ark. The seeds resulting from this controlled hybridization were germinated in a greenhouse during the winter of 1971–72. Resulting seedlings were planted in the spring of 1972 in a field on the Arkansas Agricultural Experiment Station at Clarksville, Ark. The seedlings fruited in the summer of 1974 and one, designated Ark. 1448, was selected for its outstanding fruit quality and seedless fruit.

During 1975, the original plant selection was propagated asexually by rooting hardwood cuttings and a test planting of three vines was established. Subsequently, larger test plantings have been established with asexually multiplied vines at three additional locations in Arkansas and on state agricultural experiment stations in Texas, New York, Missouri, North Carolina, Illinois, Florida, New Jersey, Louisiana, and South Carolina.

The new variety has been asexually propagated annually since 1975 by the rooting of both hardwood and softwood cuttings and by grafting onto rootstocks. It roots readily from both hardwood and softwood cuttings and no graft incompatibility has been observed. During all types of asexual multiplication, the vegetative and fruit characteristics of the original plant have been maintained.

Test plantings over a wide geographic area have shown this new variety to be widely adapted to differing soil and climatic conditions. It has shown average winter hardiness for a seedless grape, but may sustain wood injury at temperatures below −23° C.

Vines of the new variety are vigorous and have produced well as own-rooted plants in all locations tested except on the calcareous soils of southwest Texas, where it must be grafted onto a rootstock. Vines are precocious in bearing, and good production is obtained during the early years after planting. Due to their precocity, young vines may overproduce, resulting in uneven ripening within the clusters, and benefit from cluster thinning.

The vines and fruit of the new variety are moderately tolerant of the common fungus disease black rot (*Guignardia bidwellii* (Ell.) V. & R.), anthracnose (*Elsinoe*

*ampelina* (d.By.) Sher), and powdery mildew (*Uncinula necator* Burr.), but are susceptible to downy mildew (*Plasmopora viticola* Berl. & Tomi.). A spray program for disease control is required in humid areas.

The new variety ripens its fruit in midseason, about 2 weeks after the Venus cultivar and 1 week after the Reliance cultivar. The average ripening date in central Arkansas is July 30. The fruit quality is maintained well on the vine after maturity. Berries adhere well to the fruit pedicels and do not shatter from the clusters. The fruit has shown no inclination to split following rains.

The fruit is an attractive bright red color at maturity, The fruit shape is oval. Fruit skins are thin and adhere to the flesh. The flesh texture is very firm and crisp. The fruit is of the stenospermocarpic type of seedlessness and contains small, soft vestigial seed traces that are not noticeable when eaten. The berries are large in size for a seedless grape. The flavor is pleasingly sweet and typically vinifera in character, with no strong flavor components. Soluble solids content of the fruit is high (ca. 20%). The fresh fruit stores well for up to 12 weeks when held at 2° C. under $SO_2$ pads. This ability to be stored is far superior to the cultivars Venus, Reliance, and Mars. The fruit can be processed into an acceptable blending wine which is vinifera in character.

Fruit clusters, borne usually two per shoot, are medium in size, well-filled and of compact conical shape. Fruit cluster peduncles are short and the clusters form close to the supporting shoots.

The new variety has been named the Saturn cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject grapevine. Color terminology is in accordance with that of The Royal Horticultural Society Colour Chart published in 1966 by The Royal Horticultural Society of London, England.

Where dimensions, sizes, colors and other characteristics are given, it is to be understood that such characteristics are approximations of averages set forth as accurately as practicable.

The description reported herein are from specimens grown at Clarksville, Ark.

Vine:

*Size.*—Medium.

*Time of Bud Break.*—March 25.

*Growth.*—Medium vigor, cessation in early fall.

*Productivity.*—Medium-high (13–16 MT/ha on mature vines). Young vines precocious.

*Cold hardiness.*—Average for seedless grapes. Hardy to −23° C.

*Canes.*—Medium diameter, long, semi-upright in growth habit. Diameter of mature cane: base 10.0 mm, midpoint 6.0 mm, terminal 2.0 mm. Internode length: base 3.0 cm, midpoint 9.0 cm, terminal 4.5 cm. Color of mature cane: base, greyed-orange (166B); midpoint, greyed-orange (165B); terminal, greyed-orange (165B). Color of growing shoot in spring: base, yellow green (146C); terminal, yellow green (144A).

*Disease resistance.*—Moderate resistance to fungus diseases black rot, powdery mildew, and anthracnose; susceptible to downy mildew.

Foliage:

*Leaves.*—Color — mature leaves near base of shoot are yellow green (147A) on adaxial surface and green (139C) on abaxial surface. Sub-terminal fully expanded leaves are yellow green (147A) on adaxial surface and green (139C) on abaxial surface. Petioles are yellow green (146D) on young leaves and greyed-purple (183C) on mature leaves. Sinus of mature leaf at base of cane is 4.0 cm deep and 4.0 cm wide at widest point. Mature leaves have no pubescence.

Flowers:

*Date of first bloom.*—June 2.

*Date of last bloom.*—June 10.

*Blossom color.*—Yellow white (158D).

*Shape of cluster.*—Short conic, slight taper, occasionaly with shoulder.

*Size of cluster.*—Length: 12–18 cm, ave. 13.4 cm. Width: 10–15 cm, ave. 10.7 cm. Weight: ave. 236 g. Character: compact, well-filled. Number of berries: 95.

*Reproductive organs.*—Stamens — medium and erect. Pistils — medium long. Pollen — normal. Type of seedlessness — stenospermocarpy.

Fruit:

*Maturity.*—Midseason, 7 days later than Reliance. Average ripe date July 30.

*Size of berry.*—Medium-large, ave. 3.0 g, larger than Reliance and Canadice, uniform in size; length 2.1 cm, diameter at base 0.9 cm, equator 1.7 cm, apex 0.7 cm.

*Shape.*—Oval, uniform shape.

*Color.*—Red at maturity (Greyed-purple Group (187A).

*Skin.*—Thin, adhering to flesh.

*Character of seeds.*—Stenospermocarpic seedless, very small vestigial seeds present but not lignified and unnoticeable when eaten.

*Flesh.*—Very firm texture.

*Flavor.*—Typically vinifera, sweet, no strong flavor components.

*Soluble solids.*—20%.

*Total acids.*—0.51%.

*pH.*—3.55.

*Eating quality.*—Excellent.

*Storage quality.*—Very good.

*Berries per cluster.*—95.

*Clusters per vine.*—56.

*Clusters per shoot.*—Usually 2.

*Uses.*—Fresh dessert grape, blending wine.

The variety: The most distinctive features of the variety are its unique and attractive fruit color and shape, its excellent, fruit firmness, and its ability to be stored.

I claim:

1. A new and distinct variety of grapevine, substantially as illustrated and described, characterized by its attractive red fruit color, oval fruit shape, very firm texture, and cold storage capability.

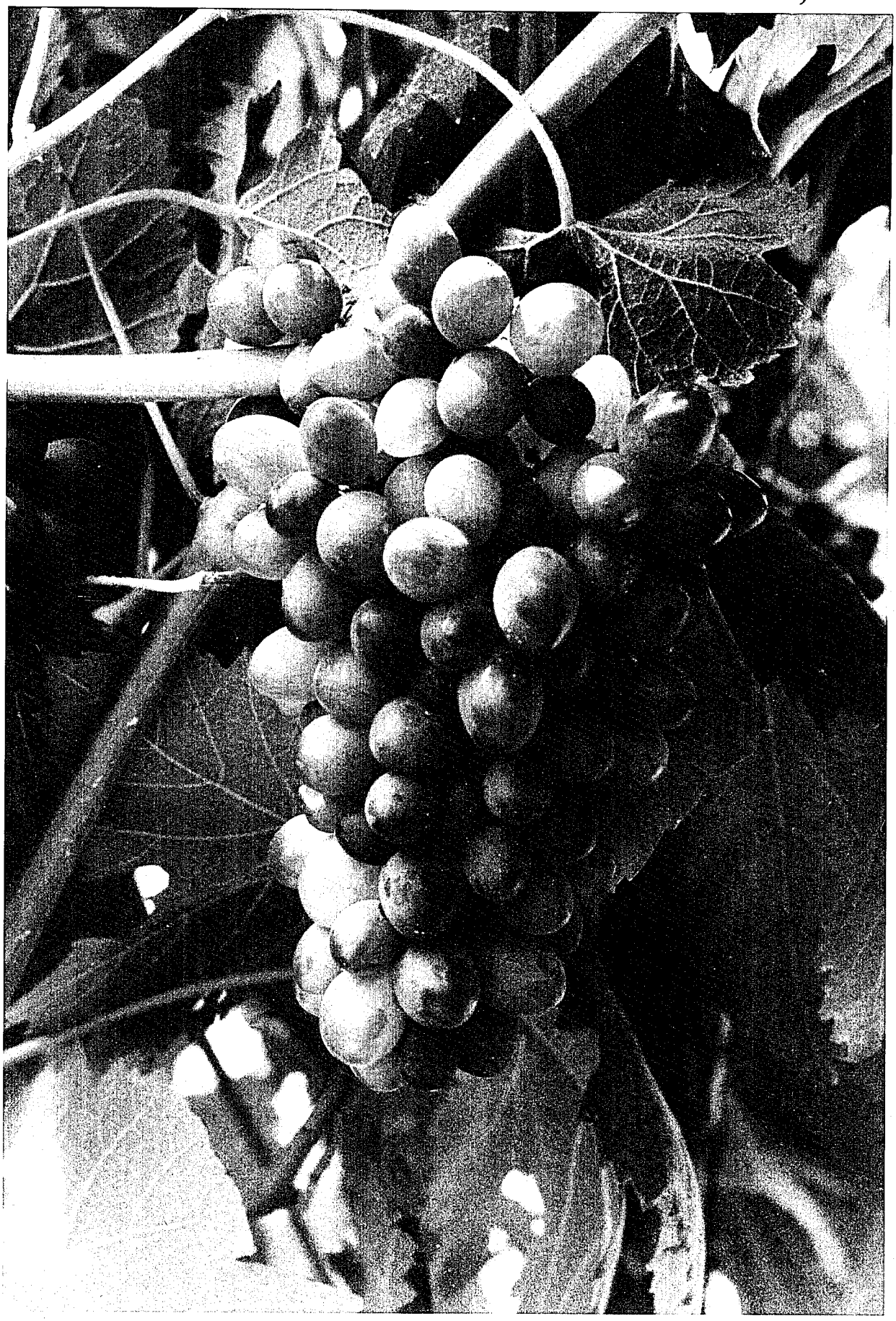

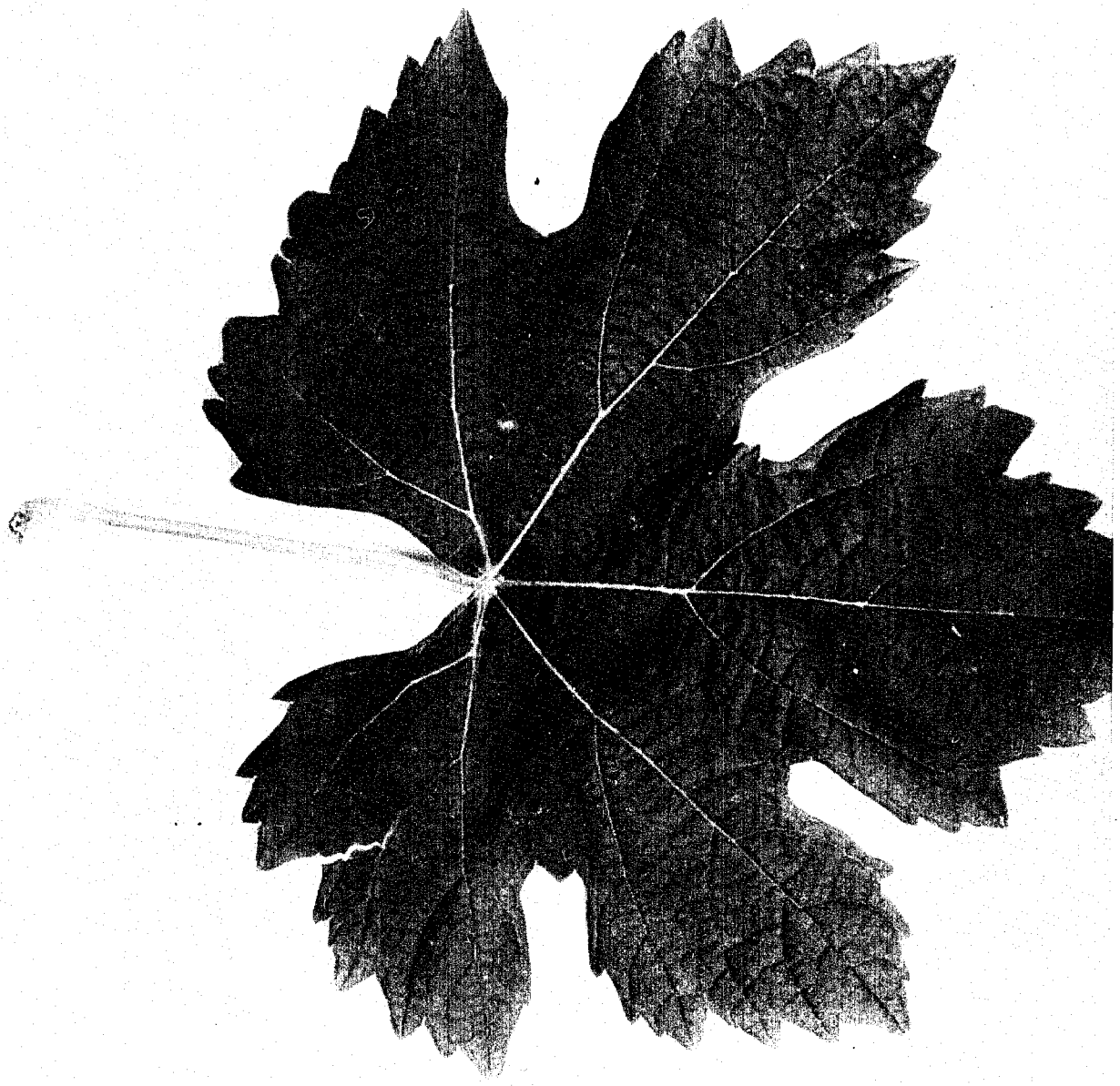

* * * * *